US010933007B2

(12) United States Patent
Mathonneau et al.

(10) Patent No.: US 10,933,007 B2
(45) Date of Patent: Mar. 2, 2021

(54) COMPOSITION COMPRISING THE COMBINATION OF SPECIFIC ALKOXYSILANES AND OF A SURFACTANT

(71) Applicant: L'OREAL, Paris (FR)

(72) Inventors: Estelle Mathonneau, Saint-Ouen (FR); Julien Cabourg, Combs la Ville (FR); Grégory Plos, Saint-Ouen (FR); Marie Cognet, Saint-Ouen (FR); Adrien Benazzouz, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/061,858

(22) PCT Filed: Dec. 14, 2016

(86) PCT No.: PCT/EP2016/081023
§ 371 (c)(1),
(2) Date: Jun. 13, 2018

(87) PCT Pub. No.: WO2017/102855
PCT Pub. Date: Jun. 22, 2017

(65) Prior Publication Data
US 2018/0369109 A1 Dec. 27, 2018

(30) Foreign Application Priority Data
Dec. 14, 2015 (FR) ...................... 1562330

(51) Int. Cl.
A61K 8/58 (2006.01)
A61K 8/41 (2006.01)
A61Q 5/02 (2006.01)
A61Q 5/12 (2006.01)
A61K 8/44 (2006.01)
A61K 8/46 (2006.01)

(52) U.S. Cl.
CPC .............. A61K 8/585 (2013.01); A61K 8/416 (2013.01); A61K 8/44 (2013.01); A61K 8/463 (2013.01); A61Q 5/02 (2013.01); A61Q 5/12 (2013.01); A61K 2800/5922 (2013.01)

(58) Field of Classification Search
None
See application file for complete search history.

(56) References Cited

U.S. PATENT DOCUMENTS

| 2,261,002 | A | 10/1941 | Ritter |
| 2,271,378 | A | 1/1942 | Searle |
| 2,273,780 | A | 2/1942 | Dittmar |
| 2,375,853 | A | 5/1945 | Kirby et al. |
| 2,388,614 | A | 11/1945 | Kirby et al. |
| 2,454,547 | A | 11/1948 | Bock et al. |
| 2,961,347 | A | 11/1960 | Floyd |
| 3,206,462 | A | 9/1965 | McCarty |
| 3,227,615 | A | 1/1966 | Korden |
| 3,632,559 | A | 1/1972 | Matter et al. |
| 3,874,870 | A | 4/1975 | Green et al. |
| 3,912,808 | A | 10/1975 | Sokol |
| 3,917,817 | A | 11/1975 | Vanlerberghe et al. |
| 3,929,990 | A | 12/1975 | Green et al. |
| 3,966,904 | A | 6/1976 | Green et al. |
| 4,001,432 | A | 1/1977 | Green et al. |
| 4,005,193 | A | 1/1977 | Green et al. |
| 4,025,617 | A | 5/1977 | Green et al. |
| 4,025,627 | A | 5/1977 | Green et al. |
| 4,025,653 | A | 5/1977 | Green et al. |
| 4,026,945 | A | 5/1977 | Green et al. |
| 4,027,020 | A | 5/1977 | Green et al. |
| 4,075,136 | A | 2/1978 | Schaper |
| 4,137,180 | A | 1/1979 | Naik et al. |
| 4,172,887 | A | 10/1979 | Vanlerberghe et al. |
| 4,197,865 | A | 4/1980 | Jacquet et al. |
| 4,217,914 | A | 8/1980 | Jacquet et al. |
| 4,240,450 | A | 12/1980 | Grollier et al. |
| 4,349,532 | A | 9/1982 | Vanlerberghe et al. |
| 4,591,610 | A | 5/1986 | Grollier |
| 4,761,273 | A | 8/1988 | Grollier et al. |
| 4,839,166 | A | 6/1989 | Grollier et al. |
| 4,874,554 | A | 10/1989 | Lange et al. |

(Continued)

FOREIGN PATENT DOCUMENTS

| EP | 0159628 A2 | 10/1985 |
| EP | 0337354 A1 | 10/1986 |

(Continued)

OTHER PUBLICATIONS

International Search Report for Application No. PCT/EP2016/081023, dated Feb. 24, 2017.
International Search Report for counterpart Application No. PCT/EP2015/077927, dated Mar. 1, 2016.
Mintel, "Hair Conditioner," XP002742867, Dec. 2013.
Mintel, "Masque for Fine Hair," XP-002742866, Jun. 2011.
Todd, Charles, et al., "Volatile Silicone Fluids for Cosmetic Formulations," Cosmetics and Toiletries, vol. 91, Jan. 1976, pp. 29-32.
Non-Final Office Action for co-pending U.S. Appl. No. 15/529,266, dated Feb. 26, 2019.

(Continued)

Primary Examiner — Robert A Wax
Assistant Examiner — Randeep Singh
(74) Attorney, Agent, or Firm — The Marbury Law Group, PLLC

(57) ABSTRACT

The invention relates to a composition comprising: (a) one or more alkoxysilanes comprising solubilizing function(s) of formula $R_1Si(OR_2)_z(R_3)_x(OH)_y$, and/or hydrolysis products thereof and/or oligomers thereof, (b) one or more of formula $(R_4)_mSi(OR_5)_n$ and/or hydrolysis products thereof and/or oligomers thereof, et (c) one or more surfactants. It also relates to the use thereof for cleansing and/or conditioning keratin fibres.

13 Claims, No Drawings

(56) References Cited

U.S. PATENT DOCUMENTS

| | | |
|---|---|---|
| 4,996,059 A | 2/1991 | Grollier et al. |
| 5,089,252 A | 2/1992 | Grollier et al. |
| 6,159,914 A | 12/2000 | DeCoster et al. |
| 6,451,747 B1 | 9/2002 | Decoster |
| 9,248,083 B2 | 2/2016 | Aires et al. |
| 2006/0110351 A1 | 5/2006 | Koehler et al. |
| 2007/0060489 A1 | 3/2007 | Sun et al. |
| 2009/0291058 A1 | 11/2009 | Woodland et al. |
| 2011/0158927 A1 | 6/2011 | Viravau et al. |
| 2012/0328542 A1* | 12/2012 | Samain .......... A61K 8/585 424/60 |
| 2013/0233331 A1 | 9/2013 | Khenniche et al. |
| 2013/0251656 A1 | 9/2013 | Khenniche et al. |
| 2014/0314696 A1* | 10/2014 | Kergosien .......... A61Q 1/04 424/61 |
| 2015/0047664 A1* | 2/2015 | Samain .......... A61K 8/365 132/202 |
| 2015/0290093 A1 | 10/2015 | Salvemini et al. |
| 2018/0369109 A1 | 12/2018 | Mathonneau et al. |

FOREIGN PATENT DOCUMENTS

| | | |
|---|---|---|
| EP | 1736139 A1 | 12/2006 |
| EP | 2111848 A2 | 10/2009 |
| EP | 2343042 A2 | 7/2011 |
| EP | 2471506 A1 | 7/2012 |
| FR | 1583363 A | 10/1969 |
| FR | 2080759 A1 | 11/1971 |
| FR | 2162025 A | 7/1973 |
| FR | 2190406 A2 | 2/1974 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2383660 A1 | 10/1978 |
| FR | 2413907 A1 | 8/1979 |
| FR | 2470596 A1 | 6/1981 |
| FR | 2505348 A1 | 11/1982 |
| FR | 2519863 A1 | 7/1983 |
| FR | 2542997 A1 | 9/1984 |
| FR | 2598611 A1 | 11/1987 |
| FR | 2910276 A1 | 6/2008 |
| FR | 2930438 A1 | 10/2009 |
| FR | 2954099 A1 | 6/2011 |
| FR | 2954100 A1 | 6/2011 |
| FR | 2954129 A1 | 6/2011 |
| FR | 2966350 A1 | 4/2012 |
| FR | 2966351 A1 | 4/2012 |
| FR | 2966352 A1 | 4/2012 |
| FR | 2999077 A1 | 6/2014 |
| GB | 1546809 A | 5/1979 |
| JP | 2002356672 A | 12/2002 |
| RU | 2150265 C1 | 6/2000 |
| RU | 2177779 C2 | 1/2002 |
| RU | 2007134258 A | 3/2009 |
| WO | 2004012691 A1 | 2/2004 |
| WO | 2009/011677 A1 | 1/2009 |
| WO | 2012/038880 A2 | 3/2012 |
| WO | 2012055805 A1 | 5/2012 |
| WO | 2012/163869 A2 | 12/2012 |
| WO | 2013/144871 A1 | 10/2013 |
| WO | 2014/124066 A1 | 8/2014 |
| WO | 2016/083578 A1 | 6/2016 |

OTHER PUBLICATIONS

Final Office Action for co-pending U.S. Appl. No. 15/529,266, dated Sep. 23, 2019.

Non-Final Office Action for copending U.S. Appl. No. 15/529,266, dated Jul. 16, 2020.

Non-Final Office Action for copending U.S. Appl. No. 16/061,796, dated Oct. 27, 2020.

* cited by examiner

COMPOSITION COMPRISING THE COMBINATION OF SPECIFIC ALKOXYSILANES AND OF A SURFACTANT

CROSS REFERENCE TO RELATED APPLICATIONS

This is a national stage application of PCT/EP2016/081023, filed internationally on Dec. 14, 2016, which claims priority to French Application No. 1562330 filed on Dec. 14, 2015, both of which are incorporated by reference herein in their entireties.

The present invention relates to a composition comprising a combination of specific alkoxysilanes and at least one surfactant, to the use thereof for the cosmetic treatment of keratin fibres and to a cosmetic treatment process using this composition.

In the field of the cosmetic treatment of keratin fibres, in particular human keratin fibres, such as the hair, maintenance of the head of hair is provided by the combination of two types of treatment:

cleansing, the function of which is to remove exogenous soiling such as dust, endogenous soiling such as sebum which migrates from the scalp along the hair shaft, and also any residues from styling products used in the leave-on mode (for instance polymers from lacquer, from gels, from mousses, fatty substances that come from hair creams, milks or oils); and care, generally carried out after the cleansing step, which can be performed according to two main modes, rinse-off (products of conditioner or mask types), or leave-on, with lotions, milks, creams, oils or pastes, the leave-on modes also having the objective of providing hair shaping.

For efficient cleansing, use is made of anionic surfactants, such as alkyl sulfates, alkyl sulfonates or alkyl ether sulfates, usually combined with surfactants of zwitterionic type such as betaines. The effective detergent action of these surfactants results, after rinsing, in a coarse, crispy feel, and in difficulties with disentangling, which may be critical for fine or curly hair or hair sensitized by the action of light or treatments such as dyeing, bleaching, permanent-waving or straightening.

In order to compensate for these drawbacks, cationic polymers and/or silicones are added to surfactant-based compositions, which cationic polymers and/or silicones are not completely removed after rinsing and make it possible to lubricate the fibres, facilitating disentangling of wet hair and of dry hair.

However, it remains difficult to simultaneously obtain a good level of cleansing and very easy disentangling and this is one of the reasons why rinse-off or leave-on care products are used.

Care products generally comprise liquid or solid fatty substances, for instance fatty alcohols or silicones, combined with cationic agents, of the following types: cationic surfactants, cationic polymers, or cationic or cationizable silicones. They are applied in rinse-off mode, for example in the case of conditioners and masks, or else in leave-on mode, for example in the case of care milks, creams or oils.

In order to improve the performances of cleansing and care products, various combinations of alkoxysilane(s) comprising solubilizing function(s) with at least one surfactant that may be specific are known from French patent application Nos. 2 930 438, 2 954 099, 2 954 100 and 2 954 129. Other combinations which also make it possible to remedy this, in particular of fatty-chain alkoxysilanes and surfactant(s), are described in French patent applications Nos. 2 966 350 and 2 966 351.

These combinations have admittedly made it possible to obtain good conditioning performances, in particular in terms of wet disentangling, of suppleness, of even feel from the roots to the end and of manageability (smooth appearance), both in the case of hair cleansing treatments and for hair care treatments.

However, the levels of performance still remain insufficient, and the persistence of these performances is not entirely satisfactory. Furthermore, the problems of stability of combinations of this type considerably limit the formulation possibilities. Moreover, the feel of the hair after treatment can appear to be unnatural.

These products are also expected to bring reinforcing effects to the head of hair, with an increase in apparent volume of the head of hair and an increase in its perceived density, most particularly for normal or fine hair, and even more if said hair has undergone treatments such as dyeing operations, bleaching operations or permanent-waving modifications of the shape thereof (curling, in certain cases, straightening) but none of the technologies proposed to date is satisfactory.

Additionally, rinse-off or leave-on care products are also used for limiting the appearance of frizziness during exposure to moisture, but they are not very effective or else they give a greasy feel and appearance.

Finally, the performances of cleansing, care or volumizing treatment products are not or not very long-lasting. In fact, as soon as the first shampooing operation takes place, there is again in particular a coarse feel and difficulty in disentangling the hair. On the one hand, this shows that the hair is still as damaged and brittle as before the treatments, and, on the other hand, this makes it necessary to reapply the care products virtually systematically.

There is thus a need to develop hair cleansing and care compositions which make it possible to clearly improve the conditioning performances, such as disentangling of wet hair, suppleness, manageability and smooth feel, and to also provide a gain in volume and in density, which are stable over time, and easy to use, while at the same time keeping a non-tacky, non-greasy natural feel, with, in the case in particular of sensitized hair, persistence of the care that is noticeable between two, or even several, shampooing operations.

The applicant has now discovered that the combined use of at least two different specific alkoxysilanes, as defined below, and of at least one surfactant makes it possible to meet this need.

A subject of the invention is thus a composition comprising:

(a) one or more alkoxysilanes comprising solubilizing function(s) of formula (I) below, and/or hydrolysis products thereof and/or oligomers thereof:

$$R_1Si(OR_2)_z(R_3)_x(OH)_y \quad (I)$$

in which:

$R_1$ is a linear or branched, saturated or unsaturated, cyclic or acyclic $C_1$-$C_6$ hydrocarbon-based chain substituted with one or more group(s) chosen from the following groups:

amine $NH_2$ or $NHR$, R being:

a $C_1$-$C_{20}$ alkyl group, preferably a $C_1$-$C_6$ alkyl group, optionally substituted with a group comprising a silicon atom, a $C_3$-$C_{40}$ cycloalkyl group or a $C_6$-$C_{30}$ aromatic group, hydroxyl, thiol, aryl or aryloxy which is substituted or unsubstituted, in particular substituted with an amino group or with a $C_1$-$C_4$ aminoalkyl group;

$R_1$ possibly being interrupted with a heteroatom such as O, S or NH, or a carbonyl group (CO), $R_2$ and $R_3$, which may be identical or different, represent a linear or branched alkyl group comprising from 1 to 6 carbon atoms, y denotes an integer ranging from 0 to 3, z denotes an integer ranging from 0 to 3, and x denotes an integer ranging from 0 to 2, with z+x+y=3, (b) one or more alkylalkoxysilanes of formula (III) below, and/or hydrolysis products thereof, and/or oligomers thereof:

$$(R_4)_m Si(OR_5)_n \qquad (III)$$

in which:

$R_4$ and $R_5$ each represent, independently of one another, a $C_{1-6}$, better still $C_{1-4}$, alkyl group such as methyl, ethyl, n-propyl, isopropyl, n-butyl, isobutyl and tert-butyl, preferably methyl, ethyl and n-propyl, n ranges from 1 to 3, m ranges from 1 to 3, on condition that m+n=4, and (c) one or more surfactants.

The compounds (a) and (b) are present in the composition described above in an (a)/(b) weight ratio ranging preferably from 0.5 to 10, more preferably from 1 to 10, and better still from 1.5 to 7.

It is used in particular for cleansing and/or conditioning keratin fibres, in particular human keratin fibres such as the hair.

This composition is stable over time, and makes it possible to obtain better cosmetic properties such as disentangling, and a non-tacky, non-greasy, natural smooth feel on wet and dry hair. In addition, persistence of the properties is observed after at least one shampooing operation. Furthermore, this composition improves the durability of dyeing effects with respect to shampoo.

The term "stable over time" is intended to mean, for the purposes of the present invention, that the visual appearance and the viscosity of the compositions do not change or do not substantially change (variation generally less than 10% relative to the viscosity at T0) over time under standard storage conditions, for example for a month or two months following production of said compositions, at 4° C., at ambient temperature (20-25° C.) and at 45° C. It is also intended to mean that the performance obtained does not change or does not substantially change during the storage of the formulae.

Another subject of the invention is constituted of a process for cosmetic treatment of, more particularly for cleansing and/or conditioning, keratin fibres, in particular human keratin fibres such as the hair, comprising the use of the composition as defined above.

A subject of the present invention is also a composition as defined above, wherein the (a)/(b) weight ratio ranges from 0.5 to 10.

Other subjects, characteristics, aspects and advantages of the invention will emerge even more clearly on reading the description and the examples that follow.

In the text that follows, and unless otherwise indicated, the limits of a range of values are included in this range, in particular in the expressions "between" and "ranging from . . . to . . . ".

The expression "at least one" used in the present description is equivalent to the expression "one or more".

According to the invention, the composition comprising:

(a) one or more alkoxysilane(s) comprising solubilizing function(s) of formula (I) as defined in the present application, and/or hydrolysis products thereof and/or oligomers thereof, (b) one or more alkylalkoxysilanes of formula (III) as defined in the present application, and/or hydrolysis products thereof and/or oligomers thereof, and (c) one or more surfactants, is used for cleansing and/or conditioning keratin fibres, in particular human keratin fibres such as the hair.

The term "oligomer" is intended to mean the polymerization products of the compounds to which the expression "oligomer" relates, comprising from 2 to 10 silicon atoms.

In the present invention, the expression "alkoxysilane(s) comprising solubilizing function(s) (a)" covers the alkoxysilane(s) comprising solubilizing function(s) of formula (I) below, and/or hydrolysis product(s) thereof and/or oligomer(s) thereof:

$$R_1 Si(OR_2)_z(R_3)_x(OH)_y \qquad (I)$$

in which:

$R_1$ is a linear or branched, saturated or unsaturated, cyclic or acyclic $C_1$-$C_6$ hydrocarbon-based chain substituted with one or more group(s) chosen from the following groups:

amine $NH_2$ or NHR, R being:

a $C_1$-$C_{20}$ alkyl group, preferably a $C_1$-$C_6$ alkyl group, optionally substituted with a group comprising a silicon atom, a $C_3$-$C_{40}$ cycloalkyl group or a $C_6$-$C_{30}$ aromatic group, hydroxyl, thiol, aryl or aryloxy which is substituted or unsubstituted, in particular substituted with an amino group or with a $C_1$-$C_4$ aminoalkyl group, $R_1$ possibly being interrupted with a heteroatom (O, S or NH) or a carbonyl group (CO), $R_2$ and $R_3$, which may be identical or different, represent a linear or branched alkyl group comprising from 1 to 6 carbon atoms, y denotes an integer ranging from 0 to 3, z denotes an integer ranging from 0 to 3, and x denotes an integer ranging from 0 to 2, with z+x+y=3.

More particularly, the alkoxysilanes comprising solubilizing function(s) (a) comprise at least one amino group in their structure.

Preferably, $R_1$ is an acyclic chain.

Preferably, $R_1$ is a linear or branched, saturated or unsaturated $C_1$-$C_6$ hydrocarbon-based chain, substituted with an amine group $NH_2$ or NHR, R being:

a $C_1$-$C_{20}$, preferably $C_1$-$C_6$, alkyl group, optionally substituted with a group comprising a silicon atom, better still a $(R_2O)_3Si$— group, a $C_3$-$C_{40}$ cycloalkyl or a $C_6$-$C_{30}$ aromatic group.

Preferably, $R_2$ represents an alkyl group comprising from 1 to 4 carbon atoms, better still a linear alkyl group comprising from 1 to 4 carbon atoms, and is preferably the ethyl group.

Preferably, $R_3$ represents an alkyl group comprising from 1 to 4 carbon atoms, better still a linear alkyl group comprising from 1 to 4 carbon atoms, and preferably represents a methyl group or an ethyl group.

Preferably, the compound of formula (I) comprises only one or two silicon atoms in its structure.

Preferably, z ranges from 1 to 3. Even more preferentially, z is equal to 3 and thus x=y=0.

Preferably, the alkoxysilane(s) comprising solubilizing function(s) (a) according to the invention is (are) chosen from 3-aminopropyltriethoxysilane (APTES), 3-amino ethyltriethoxysilane (AETES), 3-aminopropylmethyldiethoxysilane, N-(2-aminoethyl)-3-aminopropyltriethoxysilane, 3-(m-aminophenoxy)propyltrimethoxy-silane, p-aminophenyltrimethoxysilane, N-(2-aminoethylaminomethyl)-phenethyltrimethoxysilane, bis[3-(triethoxysilyl)propyl]amine, oligomers thereof, hydrolysis products thereof and a mixture of these compounds, better still from 3-aminopropyltriethoxysilane (APTES), 3-aminoethyltriethoxysilane (AETES), 3-aminopropylmethyldiethoxy-silane, N-(2-amino ethyl)-3-aminopropyltriethoxysilane, bis[3-(triethoxysilyl)propyl]amine, oligomers thereof, hydrolysis products thereof and a mixture of these compounds, and in particular the alkoxysilane(s) comprising solubilizing function(s) (a) of formula (I) is or are chosen from 3-aminopropyltriethoxysilane (APTES), oligomers thereof, hydrolysis products thereof and a mixture of these compounds.

According to one preferred embodiment, the alkoxysilane(s) comprising solubilizing function(s) (a) is or are chosen from the compounds of formula (II) below and/or hydrolysis product(s) thereof and/or oligomer(s) thereof:

$$H_2N(CH_2)_{n''}—Si(OR')_3 \quad (II)$$

in which the R' groups, which may be identical or different, are chosen from linear or branched $C_1$-$C_6$ alkyl groups and n" is an integer ranging from 1 to 6, preferably from 2 to 4.

An alkoxysilane comprising solubilizing function(s) (a) that is particularly preferred according to this embodiment is 3-aminopropyltriethoxysilane (APTES) and/or one of the hydrolysis products thereof and/or one of the oligomers thereof.

Said alkoxysilane(s) comprising solubilizing function(s) (a) used in the composition according to the invention can represent from 0.5% to 50% by weight, preferably from 1% to 20% by weight, and in particular from 2% to 15% by weight, relative to the total weight of the composition.

The second essential ingredient (b) of the composition of the invention is an alkylalkoxysilane of formula (III) below, and/or one of the hydrolysis products thereof and/or one of the oligomers thereof:

$$(R_4)_m Si(OR_5)_n \quad (III)$$

in which:

$R_4$ and $R_5$ each represent, independently of one another, a $C_{1-6}$, better still $C_{1-4}$, alkyl group such as methyl, ethyl, n-propyl, isopropyl, n-butyl, isobutyl and tert-butyl, preferably methyl, ethyl and n-propyl, n ranges from 1 to 3, m ranges from 1 to 3, on condition that m+n=4.

Preferably, $R_5$ represents a methyl, ethyl or n-propyl group, n=3 and m=1.

Preferably, the oligomers of the compounds of formula (III) are water-soluble.

By way of examples of alkylalkoxysilanes (b) that are particularly preferred, mention may in particular be made of methyltriethoxysilane (MTES), methyltripropoxysilane, oligomers thereof and hydrolysis products thereof.

In the present invention, the expression "alkylalkoxysilane(s) (b)" encompasses the alkylalkoxysilane(s) of formula (III), and/or hydrolysis product(s) thereof and/or oligomer(s) thereof.

Said alkylalkoxysilane(s) (b) used in the composition according to the invention can represent from 0.1% to 50% by weight, preferably from 0.2% to 20% by weight and in particular from 0.3% to 10% by weight, and better still from 0.3% to 5% by weight, relative to the total weight of the composition.

In one particular embodiment of the invention, these two compounds (a) and (b) are present in the composition according to the invention in an (a)/(b) weight ratio ranging from 0.5 to 10, preferably from 1 to 10, better still from 1.5 to 7.

The surfactants (c) that can be used in the composition according to the invention may be anionic, non-ionic, amphoteric or zwitterionic or cationic. Preferably, the surfactants (c) contain(s) one or more surfactants chosen from non-ionic surfactants, anionic surfactants and amphoteric or zwitterionic surfactants, one or more cationic surfactants, or mixtures thereof.

The term "anionic surfactant" is intended to mean a surfactant comprising, as ionic or ionizable groups, only anionic groups. These anionic groups are preferably chosen from —$CO_2H$, —$CO_2^-$, —$SO_3H$, —$SO_3^-$, —$OSO_3H$, —$OSO_3^-$, $H_2PO_3$, —$HPO_3^-$, $PO_3^{2-}$, $H_2PO_2$, —$HPO_2^-$, —$PO_2^{2-}$, —POH and —$PO^-$ groups.

Mention may be made, as examples of anionic surfactants which can be used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyltaurates, salts of alkyl monoesters of polyglycoside-polycarboxylic acids, acyl lactylates, alkyl glycinates, alkyl sarcosinates, alkyl carboxylates, D-galactoside-uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 40 carbon atoms and preferably from 6 to 24 carbon atoms and the aryl group denoting a phenyl or benzyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactants are in the form of salts, it (they) can be chosen from alkali metal salts, such as the sodium or potassium salt and preferably the sodium salt, the ammonium salts, the amine salts and in particular the amino alcohol salts, or the alkaline-earth metal salts, such as the magnesium salt.

Examples of amino alcohol salts that may in particular be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)-aminomethane salts.

Alkali metal or alkaline-earth metal salts and in particular the sodium or magnesium salts are preferably used.

In one particular embodiment, the anionic surfactants may be chosen from ($C_6$-$C_{24}$)alkyl sulfates, ($C_6$-$C_{24}$)alkyl ether sulfates comprising from 2 to 50 ethylene oxide units, ($C_6$-$C_{40}$)acyl sarcosinates, ($C_6$-$C_{40}$)acyl glutamates, and ($C_6$-$C_{40}$) alkyl ether carboxylic acids comprising from 2 to 50 ethylene oxide units, ($C_6$-$C_{30}$ alkyl)sulfonates, ($C_6$-$C_{30}$ alkyl)amidesulfonates, ($C_6$-$C_{30}$ alkyl)arylsulfonates, α-olefinsulfonates, paraffinsulfonates, in particular in the form of alkali metal, ammonium, amino alcohol and alkaline-earth metal salts, or a mixture of these compounds.

Better still, use is made of ($C_{12}$-$C_{20}$)alkyl sulfates, ($C_{12}$-$C_{20}$)alkyl ether sulfates comprising from 2 to 20 ethylene oxide units, ($C_6$-$C_{24}$)acyl sarcosinates, ($C_6$-$C_{24}$)acyl glutamates, and ($C_6$-$C_{24}$) alkyl ether carboxylic acids comprising from 2 to 20 ethylene oxide units, and alkylarylsulfonates in which the alkyl group is linear or branched and contains from 8 to 28, more preferably from 10 to 24, carbon atoms, such as a linear or branched dodecyl group, and the aryl group denotes a phenyl or benzyl group, more preferably a benzyl group, in particular in the form of alkali metal, ammonium, amino alcohol and alkaline-earth metal salts, or a mixture of these compounds. Even better still, preference is given to sodium lauryl sulfate, sodium lauryl ether sulfate comprising 2.2 mol of ethylene oxide, laureth-5 carboxylic acid, sodium lauroylsarcosinate, disodium cocoylglutamate, dodecylbenzenesulfonates and their salts, in particular the sodium salt, and mixtures thereof.

Examples of non-ionic surfactants that may be used in the composition according to the invention are described, for example, in the Handbook of Surfactants by M. R. Porter, published by Blackie & Son (Glasgow and London), 1991, pp. 116-178. They are in particular chosen from alcohols, α-diols and ($C_1$-$C_{20}$)alkylphenols, these compounds being polyethoxylated, polypropoxylated and/or polyglycerolated and containing at least one fatty chain comprising, for example, from 8 to 18 carbon atoms, the number of ethylene oxide and/or propylene oxide groups possibly ranging in particular from 2 to 50, and the number of glycerol groups possibly ranging in particular from 2 to 30.

Mention may also be made of condensates of ethylene oxide and of propylene oxide with fatty alcohols, polyethoxylated fatty amides preferably having from 2 to 30 ethylene oxide units, polyglycerolated fatty amides comprising on average from 1 to 5 glycerol groups, and in particular from 1.5 to 4, ethoxylated fatty acid esters of sorbitan containing from 2 to 30 ethylene oxide units, fatty acid esters of sucrose, fatty acid esters of polyethylene glycol, ($C_6$-$C_{24}$ alkyl)-mono- or -polyglycosides, N—($C_6$-$C_{24}$ alkyl)glucamine derivatives, amine oxides such as ($C_{10}$-$C_{14}$ alkyl)amine oxides or N—($C_{10}$-$C_{14}$ acyl)aminopropylmorpholine oxides, or else vegetable oils, which are optionally hydrogenated, and in particular polyethoxylated vegetable oils preferably having from 2 to 60 ethylene oxide units, better still from 10 to 50 ethylene oxide units.

The non-ionic surfactants that are particularly preferred are chosen from polyethoxylated alcohols, alcohols comprising in particular from 8 to 18 carbon atoms and the number of ethylene oxide groups ranging in particular from 2 to 50, and ($C_6$-$C_{24}$ alkyl)-mono- or -polyglycosides, and mixtures thereof.

The amphoteric or zwitterionic surfactants capable of being used in the present invention can in particular be derivatives of optionally quaternized secondary or tertiary aliphatic amines containing at least one anionic group, such as, for example, a carboxylate, sulfonate, sulfate, phosphate or phosphonate group, and in which the aliphatic group or at least one of the aliphatic groups is a linear or branched chain comprising from 8 to 22 carbon atoms.

Mention may be made in particular of ($C_8$-$C_{20}$)alkylbetaines, sulfobetaines, ($C_8$-$C_{20}$)alkylamido($C_1$-$C_6$)alkylbetaines such as cocamidopropylbetaine, and ($C_8$-$C_{20}$)alkylamido($C_1$-$C_6$)alkyl-sulfobetaines.

Mention may also be made, among the derivatives of optionally quaternized secondary or tertiary aliphatic amines capable of being employed, of the products with respective structures (IV) and (V) below:

$$R_a\text{—CONHCH}_2\text{CH}_2\text{—N}^+(R_b)(R_c)(\text{CH}_2\text{COO}^-) \quad (IV)$$
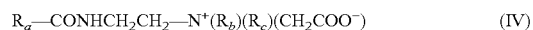

in which:
$R_a$ represents a $C_{10}$-$C_{30}$ alkyl or alkenyl group derived from an acid $R_a$—COOH preferably present in hydrolysed coconut oil, or a heptyl, nonyl or undecyl group,
$R_b$ represents a β-hydroxyethyl group, and
$R_c$ represents a carboxymethyl group;

$$R_{a'}\text{—CONHCH}_2\text{CH}_2\text{—N}(B)(B') \quad (V)$$

in which:
B represents —$CH_2CH_2OX'$,
X' represents the group —$CH_2$—COOH, —$CH_2$—COOZ', —$CH_2CH_2$—COOH, —$CH_2CH_2$—COOZ', or a hydrogen atom,
B' represents —$(CH_2)_z$—Y', with z=1 or 2,
Y' represents —COOH, —COOZ', the group —$CH_2$—CHOH—$SO_3$H or —$CH_2$—CHOH—$SO_3$Z',
Z' represents an ion derived from an alkali or alkaline-earth metal, such as sodium, potassium or magnesium; an ammonium ion; or an ion derived from an organic amine and in particular from an amino alcohol, such as monoethanolamine, diethanolamine and triethanolamine, mono isopropanolamine, diisopropanolamine or triisopropanolamine, 2-amino-2-methyl-1-propanol, 2-amino-2-methyl-1,3-propanediol and tris(hydroxymethyl)aminomethane,
$R_{a'}$ represents a $C_{10}$-$C_{30}$ alkyl or alkenyl group of an acid $R_{a'}$—COOH preferably present in coconut oil or in hydrolysed linseed oil, an alkyl group, in particular of $C_{17}$ and its iso form, or an unsaturated $C_{17}$ group.

These compounds are also classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylampho-dipropionate, disodium capryloamphodipropionate, lauroampho-dipropionic acid and cocoamphodipropionic acid.

By way of example, mention may be made of the cocoamphodiacetate sold by the company Rhodia under the trade name Miranol® $C_2M$ Concentrate.

Use may also be made of compounds of formula (Va):

$$R_{a''}\text{—NH—CH(Y''')—(CH}_2)_n\text{—C(O)—NH} \\ \text{—(CH}_2)_{n'}\text{—N(R}_d)(R_e) \quad (Va)$$
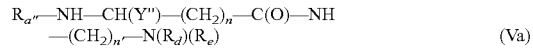

in which formula:
Y''' represents the group —C(O)OH, —C(O)OZ'', —$CH_2$—CH(OH)—$SO_3$H or the group —$CH_2$—CH(OH)—$SO_3$—Z'';
$R_d$ and $R_e$, independently of one another, represent a $C_1$-$C_4$ alkyl or hydroxyalkyl group;
Z'' represents a cationic counterion derived from an alkali metal or alkaline-earth metal, such as sodium, an ammonium ion or an ion derived from an organic amine;
$R_{a''}$ represents a $C_{10}$-$C_{30}$ alkyl or alkenyl group of an acid $R_{a''}$—C(O)OH preferably present in coconut oil or in hydrolysed linseed oil;

n and n' denote, independently of one another, an integer ranging from 1 to 3.

Mention may be made, among the compounds of formula (Va), of the compound classified in the CTFA dictionary under the name sodium diethylaminopropyl cocoaspartamide and sold by Chimex under the name Chimexane HB.

Preferably, the amphoteric or zwitterionic surfactants are chosen from ($C_8$-$C_{20}$)alkylbetaines, ($C_8$-$C_{20}$)alkylamido ($C_1$-$C_6$)alkylbetaines and ($C_8$-$C_{20}$)alkyl amphodiacetates, and mixtures thereof.

Preferentially, the amphoteric or zwitterionic surfactants are chosen, alone or as a mixture, from cocoylamidopropyl betaine, cocoyl betaine and cocoamphodiacetate.

The cationic surfactant(s) which can be used in the composition according to the invention comprise in particular salts of optionally polyoxyalkylenated primary, secondary or tertiary fatty amines, quaternary ammonium salts, and mixtures thereof.

Mention may in particular be made, as quaternary ammonium salts, for example, of:

those corresponding to the following general formula (VI):

in which the groups $R_8$ to $R_{11}$, which may be identical or different, represent a linear or branched aliphatic group comprising from 1 to 30 carbon atoms, or an aromatic group such as aryl or alkylaryl, at least one of the groups $R_8$ to $R_{11}$ comprising from 8 to 30 carbon atoms and preferably from 12 to 24 carbon atoms; and $X^-$ is an anion chosen from the group of halides such as chloride, bromide and iodide, phosphates, acetates, lactates, ($C_1$-$C_4$)alkyl sulfates, and ($C_1$-$C_4$)alkyl- or ($C_1$-$C_4$)alkylarylsulfonates.

The aliphatic groups may comprise heteroatoms such as, in particular, oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkylacetate and $C_1$-$C_{30}$ hydroxyalkyl groups, and $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Preference is given, among the quaternary ammonium salts of formula (VI), on the one hand, to tetraalkylammonium chlorides, such as, for example, dialkyldimethylammonium or alkyltrimethylammonium chlorides, in which the alkyl group comprises approximately from 12 to 22 carbon atoms, in particular behenyltrimethylammonium, distearyldimethylammonium, cetyltrimethylammonium or benzyldimethylstearylammonium chlorides, or also palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, such as, for example, those of following formula (VII):

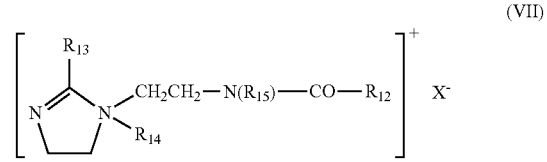

in which:

$R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

$X^-$ is an anion chosen from the group of halides such as chloride, bromide and iodide, phosphates, acetates, lactates, ($C_1$-$C_4$)alkyl sulfates, and ($C_1$-$C_4$)alkyl- or ($C_1$-$C_4$)alkylarylsulfonates.

$R_{12}$ and $R_{13}$ preferably denote a mixture of alkenyl or alkyl groups comprising from 12 to 21 carbon atoms, for example tallow fatty acid derivatives, $R_{14}$ denotes a methyl group and $R_{15}$ denotes a hydrogen atom. Such a product is, for example, sold under the name Rewoquat® W 75 by the company Rewo;

di- or triquaternary ammonium salts, in particular of following formula (VIII):

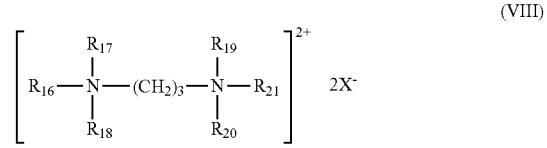

in which Rib denotes an alkyl group comprising approximately from 16 to 30 carbon atoms, which is optionally hydroxylated and/or interrupted with one or more oxygen atoms;

$R_{17}$ is chosen from hydrogen, an alkyl group comprising from 1 to 4 carbon atoms or a group —$(CH_2)_3$—$N(R_{16a})$($R_{17a}$)($R_{18a}$) or;

$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and $X^-$ is an anion chosen from the group of halides such as chloride, bromide and iodide, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate.

Such compounds are, for example, Finquat CT-P, available from Finetex (Quaternium 89), and Finquat CT, available from Finetex (Quaternium 75), quaternary ammonium salts comprising one or more ester functions, such as, for example, those of following formula (IX):

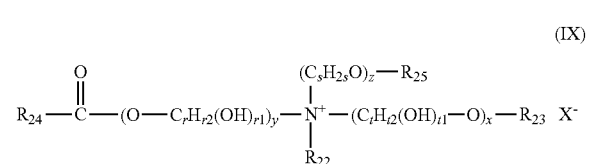

in which:

$R_{22}$ is chosen from $C_1$-$C_6$ alkyl and $C_1$-$C_6$ hydroxyalkyl or dihydroxyalkyl groups;

$R_{23}$ is chosen from:

the group

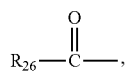

the linear or branched, saturated or unsaturated $C_1$-$C_{22}$ hydrocarbon-based groups $R_{27}$, and a hydrogen atom, $R_{25}$ is chosen from:

the group

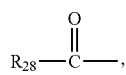

the linear or branched, saturated or unsaturated $C_1$-$C_6$ hydrocarbon-based groups $R_{29}$, and a hydrogen atom, $R_{24}$, $R_{26}$ and $R_{28}$, which may be identical or different, are chosen from linear or branched, saturated or unsaturated $C_7$-$C_{21}$ hydrocarbon-based groups;

r, s and t, which may be identical or different, are integers ranging from 2 to 6, r1 and t1, which are identical or different, have the values 0 or 1, r2+r1=2 r and t1+t2=2 t, y is an integer ranging from 1 to 10, x and z, which may be identical or different, are integers having values from 0 to 10, $X^-$ is a simple or complex, organic or mineral anion, with the proviso that the sum x+y+z is from 1 to 15, that when x is 0, then $R_{23}$ denotes $R_{27}$ and that when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are 0 or 1.

Advantageously, y is equal to 1.

Preferably, r, s and t, which may be identical or different, have the value 2 or 3 and more particularly still are equal to 2.

The anion $X^-$ is preferably a halide, preferably chloride, bromide or iodide, a ($C_1$-$C_4$)alkyl sulfate or a ($C_1$-$C_4$)alkyl- or ($C_1$-$C_4$)alkylarylsulfonate. However, use may be made of methanesulfonate, phosphate, nitrate, tosylate, an anion derived from an organic acid, such as acetate or lactate, or any other anion which is compatible with the ammonium having an ester function.

The anion $X^-$ is even more particularly chloride, methyl sulfate or ethyl sulfate.

Use is more particularly made, in the composition according to the invention, of the ammonium salts of formula (IX) in which:

$R_{22}$ denotes a methyl or ethyl group, x and y are equal to 1, z is equal to 0 or 1, r, s and t are equal to 2, $R_{23}$ is chosen from:

the group

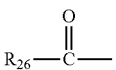

methyl, ethyl or $C_{14}$-$C_{22}$ hydrocarbon-based groups, and a hydrogen atom, $R_{25}$ is chosen from:

the group

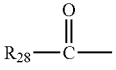

a hydrogen atom, $R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Mention may be made, for example, among the compounds of formula (IX), of diacyloxyethyldimethylammonium, diacyloxyethyl-hydroxyethylmethylammonium, monoacyloxyethyldihydroxyethyl-methylammonium, triacyloxyethylmethylammonium or monoacyloxyethylhydroxyethyldimethylammonium salts, in particular the chloride or the methyl sulfate thereof, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, alkyldiethanolamine or alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are, for example, sold under the names Dehyquart® by Henkel, Stepanquat® by Stepan, Noxamium® by Ceca or Rewoquat® WE 18 by Rewo-Witco.

The composition according to the invention may contain, for example, a mixture of quaternary ammonium monoester, diester and triester salts with a majority by weight of diester salts.

Mention may be made, as examples of such compounds, of distearoylethylhydroxyethylmethylammonium or dipalmitoylethylhydroxyethylmethylammonium salts, and in particular the methosulfates.

It is also possible to use the ammonium salts containing at least one ester function that are described in U.S. Pat. Nos. 4,874,554 and 4,137,180.

Use may also be made of behenoylhydroxypropyl-trimethylammonium chloride, for example sold by the company Kao under the name Quartamin BTC 131.

Preferably, the ammonium salts containing at least one ester function contain two ester functions.

Among the cationic surfactants, it is more particularly preferable to choose those of formula (VI) or (IX), such as the cetyltrimethylammonium, behenyltrimethylammonium or dipalmitoyl-ethylhydroxyethylmethylammonium salts, and mixtures thereof, and more particularly behenyltrimethylammonium chloride, cetyltrimethylammonium chloride or dipalmitoylethylhydroxyethylammonium methosulfate, and mixtures thereof.

In one particular embodiment of the invention, the composition comprises one or more surfactants (c) chosen from non-ionic surfactants, anionic surfactants and amphoteric or zwitterionic surfactants, and more particularly chosen from $(C_6-C_{24})$alkyl sulfates, $(C_6-C_{24})$alkyl ether sulfates comprising from 2 to 50 ethylene oxide units, $(C_6-C_{40})$acyl sarcosinates, $(C_6-C_{40})$acyl glutamates, $(C_6-C_{40})$alkyl ether carboxylic acids comprising from 2 to 50 ethylene oxide units, $(C_6-C_{30}$ alkyl)sulfonates, $(C_6-C_{30}$ alkyl)amidesulfonates, $(C_6-C_{30}$ alkyl)arylsulfonates, α-olefinsulfonates, paraffinsulfonates, in particular in the form of alkali metal, ammonium, amino alcohol and alkaline-earth metal salts; polyethoxylated $C_{8-18}$ alcohols, the number of ethylene oxide groups ranging in particular from 2 to 50, $(C_6-C_{24}$ alkyl) mono- or -polyglycosides; $(C_8-C_{20})$alkylbetaines, $(C_8-C_{20})$alkylamido$(C_1-C_6)$alkylbetaines, $(C_8-C_{20})$alkylamphodiacetates; and mixtures thereof.

In another particular embodiment of the invention, the composition comprises one or more surfactants (c) chosen from cationic surfactants, more preferentially from the cetyltrimethylammonium, behenyltrimethylammonium and dipalmitoylethylmethylammonium salts, and more particularly behenyltrimethylammonium chloride, cetyltrimethylammonium chloride, dipalmitoylethylhydroxyethylammonium methosulfate; and mixtures thereof.

In another embodiment of the invention, the composition comprises one or more surfactants (c) chosen from non-ionic surfactants, anionic surfactants and amphoteric or zwitterionic surfactants as defined above, and one or more cationic surfactants (c) as defined above.

The composition according to the invention preferably has a total content of surfactant(s) ranging from 0.5% to 40% by weight, better still from 0.5% to 30% by weight, even better still from 0.5% to 22% by weight, relative to the total weight of the composition.

Preferably, the composition according to the invention is aqueous and comprises water at a concentration preferably ranging from 5% to 98% by weight, in particular from 20% to 95% by weight and better still from 50% to 95% by weight, relative to the total weight of the composition.

The composition may also comprise one or more organic solvents that are liquid at 25° C. and $1.013 \times 10^5$ Pa and which are in particular water-soluble, such as $C_1-C_7$ alcohols, in particular $C_1-C_7$ aliphatic or aromatic monoalcohols, and $C_3-C_7$ polyols and polyol ethers, which may thus be used alone or as a mixture with water. Advantageously, the organic solvent may be chosen from ethanol and isopropanol, and mixtures thereof.

The pH of the composition, if it is aqueous, is preferably between 3 and 11 and in particular between 4 and 10.

The pH of these compositions may be adjusted to the desired value by means of basifying agents or acidifying agents that are customarily used. Among the basifying agents, examples that may be mentioned include aqueous ammonia, alkanolamines, and mineral or organic hydroxides. Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

In one preferred variant of the invention, the composition comprises at least one carboxylic acid, preferably lactic acid.

The compositions according to the invention may also contain one or more cosmetic ingredients chosen from thickeners, salts such as sodium chloride, liquid or solid fatty substances, preservatives, fragrances and dyes, and also most of the usual cosmetic agents of hair treatments, such as cationic polymers.

These additives may be present in the composition according to the invention in an amount ranging from 0 to 20% by weight, relative to the total weight of the composition.

Those skilled in the art will take care to select these optional additives and the amounts thereof so that they do not harm the properties of the compositions of the present invention.

The compositions according to the invention can be prepared in the following way: at least one alkoxysilane comprising solubilizing function(s) (a) is mixed with an amount of water at least equal to its weight, then a sufficient amount of acid to reduce the pH of the solution to a value of between 5 and 10 is added.

At least one alkylalkoxysilane (b) is mixed, in a second phase, with an amount of water at least equal to its weight, and an amount of acid sufficient to reduce the pH to a value of between 2 and 7 is also added.

The water of one of these two phases may, where appropriate, already contain one or more surfactants (c), and also one or more additives such as a thickener.

The two phases thus obtained can again be supplemented by the addition of a surfactant (c) or of another additive.

The two phases are then combined, and surfactant(s) (c) can again be added, as can one or more other additives.

The compositions according to the invention may be, in a non-limiting manner, in the form of products for washing human hair, in particular shampoos, conditioning products such as hair conditioners, or both, or masks.

The present invention also relates to a process for cosmetic treatment of, preferably for washing/cleansing and/or conditioning, keratin fibres, in particular human keratin fibres such as the hair, which consists in applying to the human hair an effective amount of a composition as described above, and optionally in rinsing it off.

A subject of the invention is also the composition as defined previously, wherein the compounds (a) and (b) are present in an (a)/(b) weight ratio ranging from 0.5 to 10, preferably from 1 to 10, better still from 1.5 to 7.

The invention is illustrated by the examples that follow.

EXAMPLES

Example 1: Care Formulations

Formulations 1 to 10 according to the invention were prepared from the ingredients indicated in the table below.

All the percentages are by weight and the amounts indicated are expressed as % by weight of product in its existing form, relative to the total weight of the formulation.

|  | 1 | 2 | 3 | 4 | 5 |
|---|---|---|---|---|---|
| Aminopropyltriethoxysilane | 5 | 5 | 10 | 10 | 10 |
| Methyltriethoxysilane | 1.5 | 1.5 | 1.5 | 1.5 | 1.5 |
| Lactic acid (90% of A.M.) | 1.75 | 3 | 2.5 | 2.5 | 3.75 |
| Cetrimonium chloride (25% of A.M.) | — | 3.2 | — | 3 | — |
| Cetearyl alcohol and dipalmitoylethylhydroxyethyl-ammonium methosulfate (30% of A.M.) (Dehyquart F30-Cognis) | — | 4.5 | — | — | — |
| Amodimethicone/trideceth-6/cetrimonium chloride (63% of A.M.) Xiameter MEM-8299 | 1 | — | 1 | 1 | 1 |
| Mineral oil | — | 3 | — | — | — |
| Cetearyl alcohol | — | 9 | — | — | — |
| Cetyl esters | — | 1 | — | — | — |
| Polyquaternium-6 (60% of A.M.) (Merquat 100-Lubrizol) | — | 1.2 | — | — | — |
| Phenoxyethanol | — | 0.2 | — | — | — |
| Chlorhexidine digluconate (20% of A.M.) | — | 0.1 | — | — | — |
| Fragrance | — | 0.8 | — | — | — |
| Water qs | 100 | 100 | 100 | 100 | 100 |

|  | 6 | 7 | 8 | 9 | 10 |
|---|---|---|---|---|---|
| Aminopropyltriethoxysilane | 10 | 10 | 10 | 10 | 5 |
| Methyltriethoxysilane | 1.5 | 3 | 3 | 3 | 1.5 |
| Lactic acid (90% of A.M.) | 3.75 | 3.5 | 4 | 4 | 2 |
| Cetrimonium chloride (25% of A.M.) | 3 | — | — | — | — |
| Behentrimonium chloride (80% of A.M.) | — | — | — | — | 1 |
| Amodimethicone/trideceth-6/cetrimonium chloride (63% of A.M.) Xiameter MEM-8299 | 1 | 1 | 1.5 | 1.5 | 1.5 |
| Cetearyl alcohol | — | — | 5 | 5 | 5 |
| Cetyl esters | — | — | 1 | 1 | 1 |
| Polyquaternium-37/mineral oil/ppg-1 trideceth-6 (Salcare SC95-BASF) | — | — | — | 1 | — |
| Starch acetate | — | — | 1 | — | — |
| Hydroxyethylcellulose | — | — | — | — | 1 |
| Phenoxyethanol | — | — | 0.5 | 0.5 | 0.5 |
| Fragrance | — | — | 0.5 | 0.5 | — |
| Beheneth-10 | — | — | 1 | 1 | — |
| Water qs | 100 | 100 | 100 | 100 | 100 |

A.M.: Active material

The compositions were obtained in the following way:

the liquid or molten fatty substances were added to a hot aqueous solution of the surfactants and preservatives. A dispersion of fatty substances was thus obtained;

separately, on the one hand, the methyltriethoxysilane was mixed with water and a sufficient amount of pH agent to obtain a pH of 3, and, on the other hand, the aminopropyltriethoxysilane was mixed with water and the remaining amount of pH agent. Once these two phases were homogeneous, they were combined. Where appropriate, the thickener was added thereto and then, after the viscosity of the mixture became constant, this mixture was combined with the fatty substance dispersion. The optional dispersions of silicones and of polyquaternium were added.

Wet locks, washed beforehand with a shampoo, were treated with formulation 10, applied in a proportion of 150 mg per gram of hair over the entire length of the lock (leave-on mode).

The lock was massaged between the fingers. Very good easy disentangling and a smooth feel of the hair were then observed.

The hair was then dried, and easy disentangling and a smooth, non-greasy and non-tacky feel were again observed.

The locks were then exposed for 24 hours to a relative humidity of 80% at 25° C. They were seen to exhibit little swelling and frizziness.

The persistence of the effects was observed by re-wetting the hair and shampooing, after which the disentangling and feel observations were repeated: the disentangling remained clearly facilitated both in the wet state and in the dry state, and the locks were smoother to the touch.

Example 2: Cleansing Formulations

Formulations 11 to 35 according to the invention were prepared from the ingredients indicated in the table below. All the percentages are by weight and the amounts indicated are expressed as % by weight of product in its existing form, relative to the total weight of the formulation.

|  | 11 | 12 | 13 | 14 | 15 | 16 | 17 | 18 |
|---|---|---|---|---|---|---|---|---|
| Aminopropyltriethoxysilane | 10 | 5 | 5 | 10 | 10 | 10 | 10 | 10 |
| Methyltriethoxysilane | 3 | 1.5 | 1.5 | 1.5 | 3 | 3 | 1.5 | 1.5 |
| Lactic acid (90% of A.M.) | 1.875 | 1.25 | 2.05 | 2.5 | 2.5 | 6 | 4 | 2.5 |
| Sodium lauryl sulfate (29% of A.M.) | — | 10 | 10 | 10 | 10 | 10 | 4 | 12 |
| Sodium laureth sulfate (70% of A.M.) | 14 | 16 | 16 | 16 | 16 | 16 | 16 | 18 |
| Cocobetaine (30% of A.M., NaCl 6.5%) | — | 11.5 | — | 11.5 | 11.5 | 11.5 | 8.5 | 2 |
| Cocamidopropylbetaine (7% of A.M., 38%, NaCl) | 15 | — | 9 | — | — | — | — | — |
| Cocoglucoside (52% of A.M.) | — | — | 8 | — | — | — | — | — |
| Sodium chloride | — | 2 | 4 | 4 | 4 | 4 | 3.2 | 4 |

-continued

| | | | | | | | | |
|---|---|---|---|---|---|---|---|---|
| Methylchloroisothiazolinone (1.125% of A.M.)/ methylisothiazolinone (0.375% of A.M.)- Kathon CG (Rohm & Haas) | — | — | — | 0.09 | 0.09 | 0.09 | — | — |
| pH | 9 | 9 | 5 | 9 | 9 | 5 | 5 | 9 |
| Water qs | 100 | 100 | 100 | 100 | 100 | 100 | 100 | 100 |

| | 19 | 20 | 21 | 22 | 23 | 24 | 25 | 26 |
|---|---|---|---|---|---|---|---|---|
| Aminopropyltriethoxysilane | 10 | 10 | 10 | 10 | 10 | 10 | 10 | 10 |
| Methyltriethoxysilane | 1.5 | 1.5 | 1.5 | 1.5 | 1.5 | 1.5 | 1.5 | 3 |
| Lactic acid (90% of A.M.) | 2.5 | 2.5 | 2.5 | 2.5 | 2.5 | 2.5 | 2.5 | 2.5 |
| Sodium lauryl sulfate (29% of A.M.) | 7 | 6 | 3 | 2 | 12 | 11 | 8 | 10 |
| Sodium laureth sulfate (70% of A.M.) | 16.4 | 8.4 | 10 | 14.6 | 8.4 | 16.4 | 14.8 | 16.1 |
| Cocobetaine (30% of A.M., NaCl 6.5%) | 13.7 | 12.4 | 9.8 | 2 | 15 | 5.9 | 12.4 | 11.5 |
| Sodium chloride | 2 | 3.6 | 2 | 4 | 4 | 2 | 3.6 | 2 |
| pH | 9 | 9 | 9 | 9 | 9 | 9 | 9 | 9 |
| Water qs | 100 | 100 | 100 | 100 | 100 | 100 | 100 | 100 |

| | 27 | 28 | 29 | 30 | 31 | 32 | 33 |
|---|---|---|---|---|---|---|---|
| Aminopropyltriethoxysilane | 10 | 10 | 2.5 | 5 | 5 | 5 | 5 |
| Methyltriethoxysilane | 3 | 3 | 0.38 | 0.75 | 0.75 | 0.75 | 0.75 |
| Lactic acid (90% of A.M.) | 2.5 | 2.5 | 0.63 | 3 | 2.05 | 2.05 | 2.25 |
| Sodium lauryl sulfate (29% of A.M.) | — | — | 10 | 10 | 4 | 10 | 9 |
| Sodium laureth sulfate (70% of A.M.) | 16 | — | 16 | 16 | 16.4 | 16 | 16 |
| Cocobetaine (30% of A.M., NaCl 6.5%) | — | 11.5 | 11.5 | 11.5 | 8.5 | — | — |
| Cocamidopropylbetaine (38% of A.M., NaCl 7%) | — | — | — | — | — | 9 | 4 |
| Cocoglucoside (52% of A.M.) | — | — | 8 | 8 | 8 | 8 | 10 |
| Sodium chloride | 6 | — | 4 | 2 | 3.2 | 4 | 4 |
| Methylchloroisothiazolinone (1.125% of A.M.)/ methylisothiazolinone (0.375% of A.M.)- Kathon CG (Rohm & Haas) | — | — | 0.09 | 0.09 | 0.09 | 0.09 | — |
| Polyquaternium-30 (22% of A.M. in water/ethanol) (Mexomere PX - Chimex) | — | — | — | 1 | — | — | — |
| Hydroxypropyl guar hydroxypropyltrimonium chloride (Jaguar C162 - Solvay) | — | — | — | 0.25 | — | — | — |
| Fragrance | — | — | — | — | — | 0.5 | — |
| pH | 9 | 9 | 5 | 9 | 9 | 5 | 5 |
| Water qs | 100 | 100 | 100 | 100 | 100 | 100 | 100 |

| | 34 | 35 |
|---|---|---|
| Steareth-100/PEG-136/HDI copolymer | 3 | 3 |
| Alkyl (C8/C16) polyglucoside (1.4) | 9 | 9 |
| Disodium cocoyl glutamate | 5 | 5 |
| Polyvinylamine/N-vinylformamide | 7.7 | 7.7 |
| Aminopropyltriethoxysilane | 5 | 10 |
| Methyltriethoxysilane | 0.75 | 3 |
| Water qs | 100 | 100 |
| pH | 9 | 9 |

A.M.: Active Material

The compositions were obtained in the following way:

separately, on the one hand, the methyltriethoxysilane was mixed with water and a sufficient amount of pH agent to obtain a pH of 3, and, on the other hand, the aminopropyltriethoxysilane was mixed with water and the remaining amount of pH agent. Once these two phases were homogeneous, they were combined. They were then added to the solutions of surfactants (formulations 11-33) or to the solutions of surfactants and of anionic polymers (formulations 34 and 35). Where appropriate, the salt, the cationic polymers, the preservatives and the fragrance were then added. If necessary, an additional pH agent was added at the end of preparation in order to readjust the pH to the target value.

Various wet locks were treated with each of formulations 14, 17, 18, 22, 24 and 28, each one being applied in a proportion of 400 mg per gram of hair. The lock was massaged between the fingers and then rinsed. The lock was then wrung out between the fingers. Easy disentangling and a smooth feel of the hair were then observed.

The hair was then dried, and easy disentangling, coupled with a significant increase in the stiffness of the fibre, measured by flexion, were again observed.

Example 3

Formulation 36 according to the invention and comparative formulation 37 were prepared from the ingredients indicated in the table below. All the percentages are by weight and the amounts indicated are expressed as % by weight of active material, relative to the total weight of the formulation.

|  | 36 (Invention) | 37 (Comparative) |
|---|---|---|
| Octyltriethoxysilane (Dynasilan OCTEO-EVONIK) | — | 5 |
| Methyltriethoxy silane (MTES) | 5 | — |
| Aminopropyltriethoxysilane (XIAMETER OFS-6011 SILANE-DOW CORNING) | 5 | 5 |
| Coco glucoside (PLANTACARE 818 UP-COGNIS) | 1 | 1 |
| Hydroxyethylcellulose (Natrosol 250 HHR PC-ASHLAND) | 0.6 | 0.6 |
| Lactic acid | 2 | 2 |
| Eau | Qs 100 | Qs 100 |

The stability of both formulations was evaluated. After their preparation, they were stored for 7 days in an oven at 66° C.

After 7 days, a phase separation was observed for formulation 37 whereas formulation 36 remains homogeneous.

Therefore, formulation 36 according to the invention has an improved stability when compared to that of comparative formulation 37.

Example 4

Formulation 38 according to the invention was prepared from the ingredients indicated in the table below. All the percentages are by weight and the amounts indicated are expressed as % by weight of active material, relative to the total weight of the formulation.

| Starch acetate | 1 |
|---|---|
| Hydroxyethylcellulose | 0.2 |
| Behentrimonium chloride | 1.58 |
| Aminopropyltriethoxysilane | 3.84 |
| Methyltriethoxysilane | 1.15 |
| Cetearyl alcohol | 3.5 |
| Mixture of myristyl stearate and of myristyl palmitate (INCI name: CETYL ESTERS (and) CETYL ESTERS, sold under the commercial tradename MIRACETI by LASERSON) | 0.7 |
| Sodium dodecylbenzenesulfonate | 0.9 |
| Preservatives | 0.3 |
| Perfume | 0.8 |
| Water Qs | 100 |

Thin hair of 6 models, washed beforehand with a shampoo, was treated with formulation 38, applied in a proportion of 95 mg per gram of hair. The hair was massaged between the fingers.

The hair was then rinsed and dried.

The hair has body, volume and individualized hair is observed.

The invention claimed is:

1. A process for cleansing and/or conditioning keratin fibres, comprising the application to the keratin fibres of an effective amount of a composition comprising:
   (a) at least one alkoxysilane comprising at least one solubilizing function of formula (I) below, and/or hydrolysis products thereof and/or oligomers thereof:

   $$R_1Si(OR_2)_z(R_3)_x(OH)_y \quad (I),$$

wherein:
   $R_1$ is a linear or branched, saturated or unsaturated, cyclic or acyclic $C_1$-$C_6$ hydrocarbon-based chain substituted with one or more group(s) chosen from the following groups:
   amine $NH_2$ or NHR, R being:
   a $C_1$-$C_{20}$ alkyl group or a $C_1$-$C_6$ alkyl group, optionally substituted with a group comprising a silicon atom,
   a $C_3$-$C_{40}$ cycloalkyl group, or
   a $C_6$-$C_{30}$ aromatic group,
   hydroxyl,
   thiol,
   aryl or aryloxy which is unsubstituted or substituted with an amino group or with a $C_1$-$C_4$ aminoalkyl group;
   $R_1$ optionally being interrupted with a heteroatom chosen from O, S or NH, or a carbonyl group (CO),
   $R_2$ and $R_3$, which may be identical or different, each represent a linear or branched alkyl group comprising from 1 to 6 carbon atoms, y denotes an integer ranging from 0 to 3,
   z denotes an integer ranging from 0 to 3, and
   x denotes an integer ranging from 0 to 2,
   with the proviso that z+x+y=3,
   (b) at least one alkylalkoxysilane of formula (III) below, and/or hydrolysis products thereof, and/or oligomers thereof:

   $$(R_4)_mSi(OR_5)_n \quad (III),$$

wherein:
   $R_4$ and $R_5$ each represent, independently of one another, a $C_{1-6}$ or $C_{1-4}$ alkyl group, or a methyl, ethyl, n-propyl, isopropyl, n-butyl, isobutyl, or tert-butyl group, n ranges from 1 to 3,
m ranges from 1 to 3,
with the proviso that m+n=4, and
(c) at least one surfactant,
wherein the (a)/(b) weight ratio ranges from 1 to 10; and optionally rinsing off the composition.

2. The process according to claim 1, wherein $R_1$ is a linear or branched, saturated or unsaturated $C_1$-$C_6$ hydrocarbon-based chain, substituted with an amine group $NH_2$ or NHR, R being:
- a $C_1$-$C_{20}$ or $C_1$-$C_6$, alkyl group, optionally substituted with a group comprising a silicon atom, or a $(R_2O)_3Si$— group,
- a $C_3$-$C_{40}$ cycloalkyl, or
- a $C_6$-$C_{30}$ aromatic group.

3. The process according to claim 1, wherein $R_2$ represents an alkyl group comprising from 1 to 4 carbon atoms.

4. The process according to claim 1, wherein the at least one alkoxysilane comprising at least one solubilizing function (a) is chosen from 3-aminopropyltriethoxysilane (APTES), 3-aminoethyltriethoxysilane (AETES), 3-aminopropyl-methyldiethoxysilane, N-(2-aminoethyl)-3-aminopropytriethoxysilane, bis[3-(triethoxysilyl)propyl]amine, oligomers thereof, hydrolysis products thereof, or mixtures thereof.

5. The process according to claim 1, wherein the at least one alkoxysilane comprising at least one solubilizing function (a) is chosen from those of formula (II) and/or hydrolysis products thereof, and/or oligomers thereof:

$$H_2N(CH_2)_{n''}-Si(OR')_3 \quad (II),$$

wherein the R' groups, which may be identical or different, are each chosen from linear or branched $C_1$-$C_6$ alkyl groups and n" is an integer ranging from 1 to 6 or from 2 to 4.

6. The process according to claim 1, wherein the at least one alkoxysilane comprising at least one solubilizing function (a) is present in an amount ranging from 0.5% to 50% by weight, relative to the total weight of the composition.

7. The process according to claim 1, wherein in formula (III), $R_5$ represents a methyl, ethyl or n-propyl group; n=3; and m=1.

8. The process according to claim 1, wherein the at least one alkylalkoxysilane (b) is chosen from methyltriethoxysilane (MTES), methyltripropoxysilane, oligomers thereof, or hydrolysis products thereof.

9. The process according to claim 1, wherein the at least one alkylalkoxysilane (b) is present in an amount ranging from 0.1% to 50% by weight, relative to the total weight of the composition.

10. The process according to claim 1, wherein the (a)/(b) weight ratio ranges from 1.5 to 7.

11. The process according to claim 1, wherein the at least one surfactant (c) is chosen from anionic surfactants; nonionic surfactants; amphoteric surfactants; zwitterionic surfactants; ($C_6$-$C_{24}$)alkyl sulfates; ($C_6$-$C_{24}$)alkyl ether sulfates comprising from 2 to 50 ethylene oxide units; ($C_6$-$C_{40}$)acyl sarcosinates; ($C_6$-$C_{40}$)acyl glutamates; ($C_6$-$C_{40}$)alkyl ether carboxylic acids comprising from 2 to 50 ethylene oxide units; ($C_6$-$C_{30}$ alkyl)sulfonates; ($C_6$-$C_{30}$ alkyl)amidesulfonates; ($C_6$-$C_{30}$ alkyl)arylsulfonates; α-olefinsulfonates; paraffinsulfonates; surfactants in the form of alkali metal, ammonium, amino alcohol and alkaline-earth metal salts; polyethoxylated $C_{8-18}$ alcohols, the number of ethylene oxide groups ranging from 2 to 50; ($C_6$-$C_{24}$ alkyl)mono- or -polyglyco sides; ($C_8$-$C_{20}$)alkylbetaines; ($C_8$-$C_{20}$)alkylamido($C_1$-$C_6$)alkylbetaines; ($C_8$-$C_{20}$)alkylamphodiacetates; or mixtures thereof.

12. The process according to claim 1, wherein the at least one surfactant (c) is chosen from cationic surfactants; cetyltrimethylammonium, behenyltrimethylammonium or dipalmitoylethylhydroxyethyl-methylammonium salts; behenyltrimethylammonium chloride, cetyltrimethylammonium chloride, dipalmitoylethylhydroxyethylammonium methosulfate, or mixtures thereof.

13. The process according to claim 1, wherein the at least one surfactant (c) is or are present in an amount ranging from 0.5% to 40% by weight, relative to the total weight of the composition.

* * * * *